United States Patent [19]
Pannetier

[11] Patent Number: 5,795,455
[45] Date of Patent: Aug. 18, 1998

[54] METHOD FOR DETERMINING THE NUCLEOTIDE SIZE OF DNA FRAGMENTS

[75] Inventor: Christophe Pannetier, Paris, France

[73] Assignees: Institut National de la Sante et de la Recherche Medicale (INSERM); Institut Pasteur, both of Paris, France

[21] Appl. No.: 801,096

[22] Filed: Feb. 14, 1997

Related U.S. Application Data

[63] Continuation of Ser. No. 367,174, Dec. 29, 1994, abandoned.

[30] Foreign Application Priority Data

Jul. 3, 1992 [FR] France ................................. 92 08253

[51] Int. Cl.$^6$ .......................... G01N 27/26; G01N 27/447
[52] U.S. Cl. ............................................ 204/466; 204/458
[58] Field of Search ..................................... 204/607, 608, 204/609, 610, 612, 613, 615, 616, 617, 618, 621, 457, 458, 459, 461, 462, 465, 466, 467

[56] References Cited

U.S. PATENT DOCUMENTS 5,030,566  7/1991  Son et al. .................................. 435/91

OTHER PUBLICATIONS

A.V. Carrano et al, "A High-Resolution, Fluoreescence-Based, Semiautomated Method for DNA Fingerprinting" Genomics 4 (1989) 129–136.

P. Eric Mayrand et al, "The use of fluorescence detection and internal lane standards to size PCR products automatically" Applied and Theoretical Electrophoresis (1992) 3, 1–11.

Henry E. Schaffer et al, "Improved Estimation of DNA Fragment Lengths from Agarobe Gels," Analytical Biochemistry 115 (1981) 113–122.

K. Corcoran et al, "Optimal Size Colling Methods for Electphoretic Analysis Utilizing Internal Size Standards" Advances in Forensic Haemogenetics, 4, (1992) 166–168.

Richard C. Parker et al, "Mapping of closed circular DNAs by cleavage with restriction endonucleases and calibration by agarose gel electrophoresis", Proceedings of the National Academy of Science, USA, vol. 74, No. 3 (Mar. 1977) 851–855.

Brian D. Plikaytis et al, "Robust Estimation of Standard Curves for Protein Molecular Weight and Linear–Duplex DNA Base–Pair Number after Gel Electrophoresis" Analytical Biochemistry, vol. 152, No. 2 (Feb. 1986) 346–364.

Henry E. Schaffer, "Chapter 1, Determination of DNA Fragment Size from Gel Electrophoresis Mobility" Statistical analysis of DNA sequence data (1983) 1–14.

Ronald G. Duggleby et al, "A Computer Program for Determining the Size of DNA Restriction Fragments," Analytical Biochemistry, vol. 110, No. 1 (Jan. 1981) 49–55.

*Primary Examiner*—William H. Beisner
*Assistant Examiner*—John S. Starsiak, Jr.
*Attorney, Agent, or Firm*—Blakely Sokoloff Taylor & Zafman

[57] ABSTRACT

A method for determining the nucleotide size of DNA fragments separated by gel electrophoresis, comprising the steps of (i) measuring the migration time of each detected DNA fragment, and (ii) correlating the size of each detected DNA fragment with its migration time.

20 Claims, 5 Drawing Sheets

METHOD FOR DETERMINING THE NUCLEOTIDE SIZE OF DNA FRAGMENTS

This is a continuation of application Ser. No. 08/367,174 filed Dec. 29, 1994 now abandoned.

The present invention relates to a method which makes it possible to determine the nucleotide size of DNA fragments.

The method in accordance with the present invention exploits a process for the separation of DNA fragments by gel electrophoresis.

The separation and detection of labeled DNA fragments, for example labeled with fluorescent markers, by gel electrophoresis, are well known to persons skilled in the art.

Various pieces of equipment capable of performing these functions are known on the market. Among these known pieces of equipment, there may be mentioned the automated gel electrophoresis device for automatic DNA sequencing marketed by the company Applied Biosystem under the reference 373A. This device is described in the document U.S. Pat. No. 4,811,218.

The known equipments for the separation of DNA fragments by gel electrophoresis generally comprise:

- a flat support for migration consisting of a gel, made of polyacrylamide or agarose for example, capable of receiving previously labeled DNA samples,
- a high-voltage continuous power supply source, typically from 1000 to 1500V, connected between the ends of the supporting gel in order to induce the separation of the DNA fragments by electrophoresis,
- a set for detection of the DNA fragments migrating successively on the supporting gel, placed at the base of the latter and
- a set for recording and processing the data derived from the detection set.

The DNA samples are prepared according to various techniques well known to persons skilled in the art.

These known preparation techniques generally use a method for the enzymatic amplification in vitro of single-stranded or double-stranded DNA nucleic acid sequences, especially by PCR (Polymerase Chain Reaction) or by the SDA (Strand Displacement Amplification) technique.

The amplification techniques in vitro, especially by PCR or SDA, have been described in the literature. There may be mentioned in particular the publications EP-A-201 184 and EP-A-200 362 on the basic technique for the PCR method. The so-called SDA (Strand Displacement Amplification) amplification technique was described during the San Diego conference on Nucleic Acids on 20–22 Nov. 1991.

In these enzymatic DNA amplification methods, the amplification of the sequence is carried out by successive cycles.

Each cycle comprises several stages:

- a stage for hybridization of specific oligonucleotide primers to the 5' ends of the DNA fragments which are complementary with them, and
- a stage for extension from the 3' ends of the primers with the aid of a DNA polymerase.

The multiplication factor for the DNA fragments is in theory two at each cycle.

In the PCR-type enzymatic DNA amplification techniques, the samples are heat-denatured at the end of each cycle. The use of a thermostable polymerase, Taq polymerase, has made it possible to develop automatic cyclers (thermal denaturation/annealing/enzymatic polymerization) whose various stages differ only in their operating temperature. The denaturing conditions generally correspond to a rise in the temperature of the reaction medium above 90° C., the annealing generally takes place between 50° and 70° C. and the extension by DNA polymerase can be carried out at relatively high temperatures, of the order of 70° C. if heat-stable DNA polymerase is used.

On the other hand, under other enzymatic DNA amplification techniques, such as the SDA technique, the products obtained at the end of each cycle are not heat-denatured. They are isothermic methods.

The SDA amplification method is based on the use of oligonucleotide primers modified in 5' by the addition of a DNA sequence recognized by a restriction enzyme, for example the enzyme Hinc II. The process requires the formation of a thiolated restriction site by incorporation of sulfur-containing deoxyadenosine triphosphate, and the alternate actions of the said Hinc II enzyme which partially hydrolyzes (on a single strand), the said restriction site, and DNA polymerase which synthesizes from a hydrolysis point a new strand, with simultaneous displacement of the previously cut nucleic sequence, without the denaturation being necessary. The annealing of the modified primers to the target requires only a first stage of denaturation of the DNA. The reaction then occurs at 37° C.

The labeling of the fragments is generally carried out with the aid of a few additional amplification cycles in the presence of primer oligonucleotides exhibiting radioactive labeling, enzymatic labeling or preferably fluorescent labeling based on fluorophores.

The migration-supporting gel generally comprises several parallel lanes, for example 24 lanes.

In the preferred case of fluorescent labeling based on fluorophores, the detection set comprises a system for excitation (for example laser or halogen lamp) and a sensor sensitive to the fluorescent radiation generated by the excited sample. In some devices, a set of mirrors placed on a carriage affording reciprocating translational movement opposite the base of the gel successively scans various lanes, reflects the excitation radiation onto the sample and returns the fluorescent radiation to the sensor.

In other devices, the excitation radiation is directly sent into the thickness of the gel, perpendicularly to the direction of electrophoresis and parallel to the plane of the gel, whereas a series of sensors collect the fluorescence signal.

The sensor delivers a signal whose amplitude is proportional to the concentration of the fluorescent color detected, provided that this amplitude remains less than a certain threshold.

Moreover, for certain devices, the simultaneous use of four fluorophores of different "colors" is known, which makes it possible to place four differently labeled samples in each lane.

For that, it is simply necessary to have a set of motorized filters, for example a wheel with four filters moved sequentially, upstream of the sensor, so as to detect successively each of the radiations and consequently to detect each of the samples.

The present invention can for example find application in a method for describing the repertoires of the immune system.

This process is essentially characterized in that
starting with a biological sample, reverse transcription of the mRNAs which it contains is carried out,
there is then carried out, on the product of transcription (or directly on the DNA extracted from the sample), separate amplifications for each primer pair V, C, V corresponding to a variable segment of the repertoire in question and C annealing with the constant segment of the repertoire studied, on each of these amplification products there is carried out, for each segment J of the repertoire, labeled, an extension step using as primer an oligonucleotide specific for this segment J and the amplification product as template, for each extension product corresponding to a triplet V,C,J thus obtained, the size and the quantity of the various extension products are shown, the description of the repertoire is carried out for each element of the repertoire corresponding to a triplet V,C,J and to the size of the element by the measurement of the quantity of this element in the said repertoire.

The present invention can also find application in a method for determining the quantity of a DNA fragment of interest by a quantitative amplification method.

This process is essentially characterized in that:

1) there is added to the sample to be analyzed containing the DNA fragment of interest, a standard DNA fragment different from the DNA fragment of interest but amplifiable by the same prime oligonucleotides, the standard DNA fragment and the DNA fragment of interest differing in sequence and/or in size by not more than about 10%, preferably by not more than 5 nucleotides per strand, 2) the DNA fragment of interest and the standard DNA fragment are co-amplified with the same prime oligonucleotides, preferably up to saturation of the amplification of the mixture of these DNA fragments, 3) there are added to the reaction medium obtained in stage 2) one or more labeled prime oligonucleotide(s), specific for the DNA fragment of interest and the standard DNA fragment, and different from the said prime oligonucleotides of stage 2), and one or more additional amplification cycles is(are) carried out with the said labeled prime oligonucleotide(s) such that, during a cycle, after denaturation of the DNA, the said labeled prime oligonucleotide(s) anneal(s) with the said fragments at an appropriate site so that extension by DNA polymerase generates labeled DNA fragments of different size and/or sequences or with different markers depending on whether they are obtained from DNA fragments of interest or standard DNA fragments respectively, then 4) the initial quantity of the DNA fragment of interest is determined as being the product of the initial quantity of standard DNA fragment and the ratio between the quantity of amplified DNA fragment of interest and the quantity of amplified standard DNA fragment, a ratio which is identical to that of the quantities of labeled DNA fragments obtained respectively from the amplified DNA fragments of interest and standard DNA fragments which are obtained in stage 3).

According to a specific embodiment, the determination of the last stage of the abovementioned method is carried out by:

separating, according to their size, by gel electrophoresis, the labeled DNA fragments obtained from the amplified DNA fragments of interest and standard DNA fragments, then by detecting the intensities of the signals corresponding to the marker for a respective primer for the labeled DNA fragments obtained from the DNA fragments of interest and standard DNA fragments respectively.

In the known equipments, the nucleotide size of the DNA fragments is evaluated in a fairly basic manner with the aid of a visual comparison of the position of the detected samples relative to the position of the labeled size standards which are codeposited on the supporting gel and subjected to the same electrophoresis as the samples to be measured.

The aim of the present invention is to improve the existing technique by proposing new means permitting a more precise measurement of the size of the DNA fragments.

This aim is achieved according to the present invention by means of a method comprising the stages which consist of:

i) measuring the migration time, over a predetermined constant length, for each detected DNA fragment, and ii) correlating the size of each detected DNA fragment with its migration time.

According to an advantageous characteristic of the present invention, the correlation between the size of each detected DNA fragment and its migration time is established based on the law:

$$L(t)=A \exp[-B/(t+t_0)]+C$$

in which A, B and C are constants, t represents the migration time, to represents a time constant and L(t) represents the length, in nucleotides of the detected DNA.

BRIEF DESCRIPTION OF THE DRAWINGS

The characteristics, aims and advantages of the present invention will emerge on reading the detailed description below, and in relation to the accompanying drawings which are given by way of non-limiting example and in which.

As indicated above, the method in accordance with the present invention, designed to determine the nucleotide size of DNA fragments, exploits a process for separating DNA fragments by gel electrophoresis.

This separation process known per se and recalled above in its essential characteristics will not be described in any further detail in the text which follows.

More specifically, the present invention exploits a process according to which standards of known size are codeposited on the supporting gel. Preferably, standards of known size are thus deposited on three control lanes, namely on the two side edges of the supporting gel and in the center thereof.

The number n of size standards thus codeposited on each control lane of the supporting gel can be chosen in any manner by the user. However, preferably, five size standards are deposited on each control lane.

By way of non-limiting example, these five standards of known size may comprise 96, 114, 140, 157 and 176 nucleotides respectively.

Figure 1:
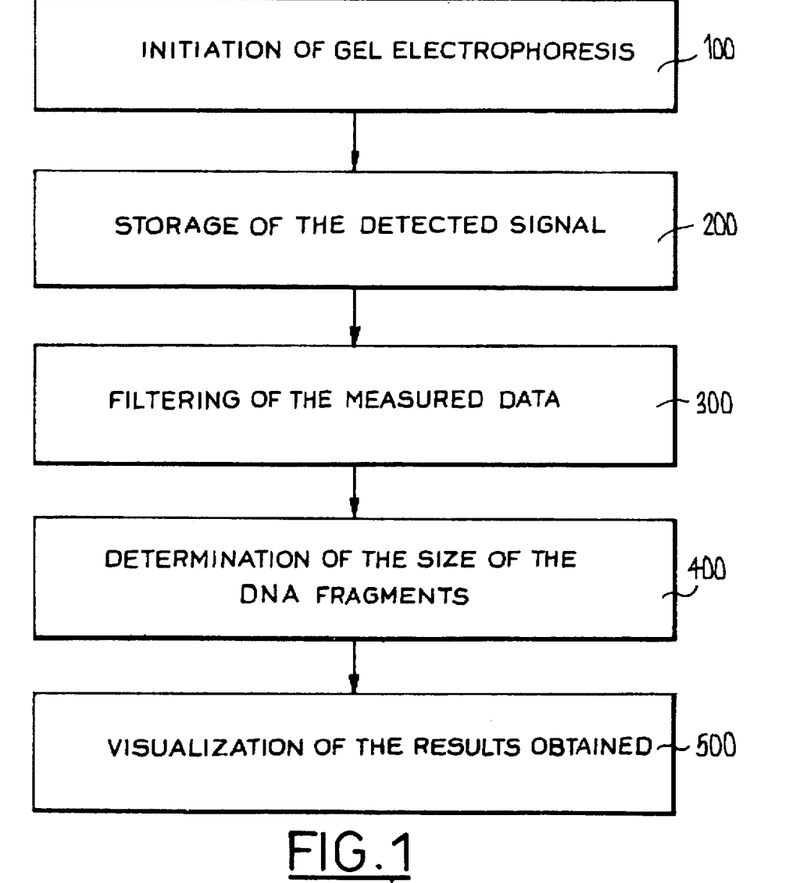
FIG. 1 represents a general schematic flow diagram of the method in accordance with the present invention.

As schematically represented in the accompanying FIG. 1, the method in accordance with the present invention preferably comprises the stages consisting of:

a) carrying out a gel electrophoresis of labeled DNA samples and of labeled size standards codeposited on the gel (stage 100 in FIG. 1), b) detecting and storing the signal derived from the sensor of the detection set (stage 200 in FIG. 1), c) filtering the measured data (stage 300 in FIG. 1), d) determining the size of the detected DNA fragments (stage 400 in FIG. 1), and e) visualizing the results obtained (stage 500 in FIG. 1).

Where appropriate, the filtering stage 300 can be carried out before the storing stage 200.

Preferably, at stage 200, the curves derived from the sensor are stored in a respective specific file at the rate of one file per measurement lane.

Figure 2:
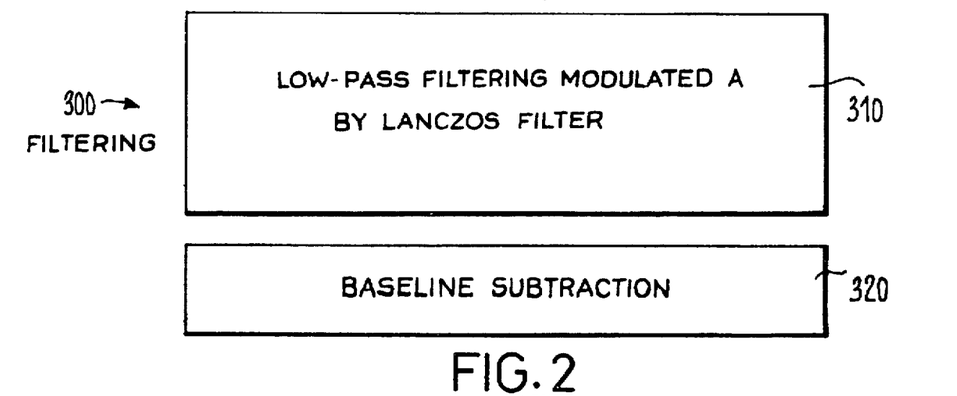
FIGS. 2 to 7 represent in the form of flow diagrams specific stages of this method.

The filtering phase 300 preferably comprises, as schematically represented in FIG. 2, the initial stage 210 of low-pass filtering modulated by a Lanczos convolution, so as to eliminate high-frequency noise, with the aid of a filter preferably having an adjustable cutoff frequency and an adjustable window width.

The width of the Lanczos window is also adjustable.

Finally, the filtering phase 300 comprises the final stage 320 for subtraction of the base line obtained at any point, as minimum value of the filtered curve, over a determined window value.

The width of this window should of course be considerably greater than the width of a peak; preferably, the width of this window is adjustable.

Stage 400 for the determination of the size of the detected DNA fragments will now be described.

As mentioned above, according to the invention, the principal stage for the determination of the size of the DNA fragments consists, after having measured the migration time of each detected DNA fragment, in correlating the size L of each detected DNA fragment with its migration time with the aid of the equation:

$$L(t) = A \exp[-B/(t+t_0)] + C$$

in which A, B and C are constants, t represents the migration time and $t_0$ represents a time constant.

It will be noted that $t_0=0$ when the time origin of the measurement coincides with the beginning of the electrophoresis.

Figure 3:
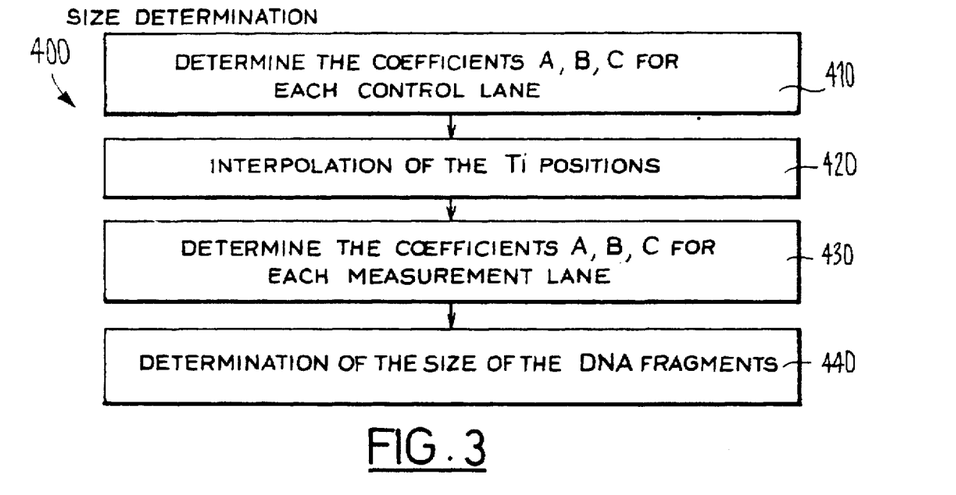

More precisely, as schematically represented in FIG. 3, stage 400 consists in:

a) determining the coefficients A, B, C for each control lane containing size standards (stage 410 in FIG. 3), whose migration times $t_i$ were measured, b) interpolating migration times $t_i$ measured in control lanes, for the measurement lanes (stage 420 in FIG. 3), c) from this interpolation, determining, for each measurement lane the value of the parameters A, B and C (stage 430 in FIG. 3)

d) determining the size of the DNA fragments based on the abovementioned law (stage 440 in FIG. 3) established for each of the gel lanes.

Figure 4:
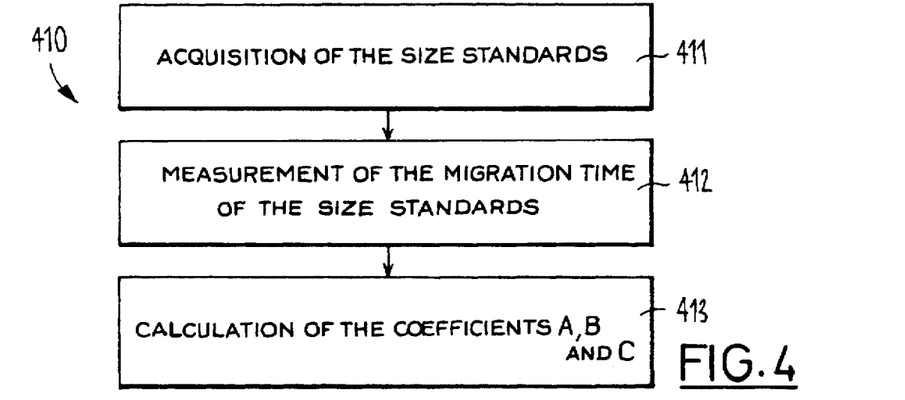

Stage 410 is illustrated in the form of a flow diagram in FIG. 4.

Figure 5:
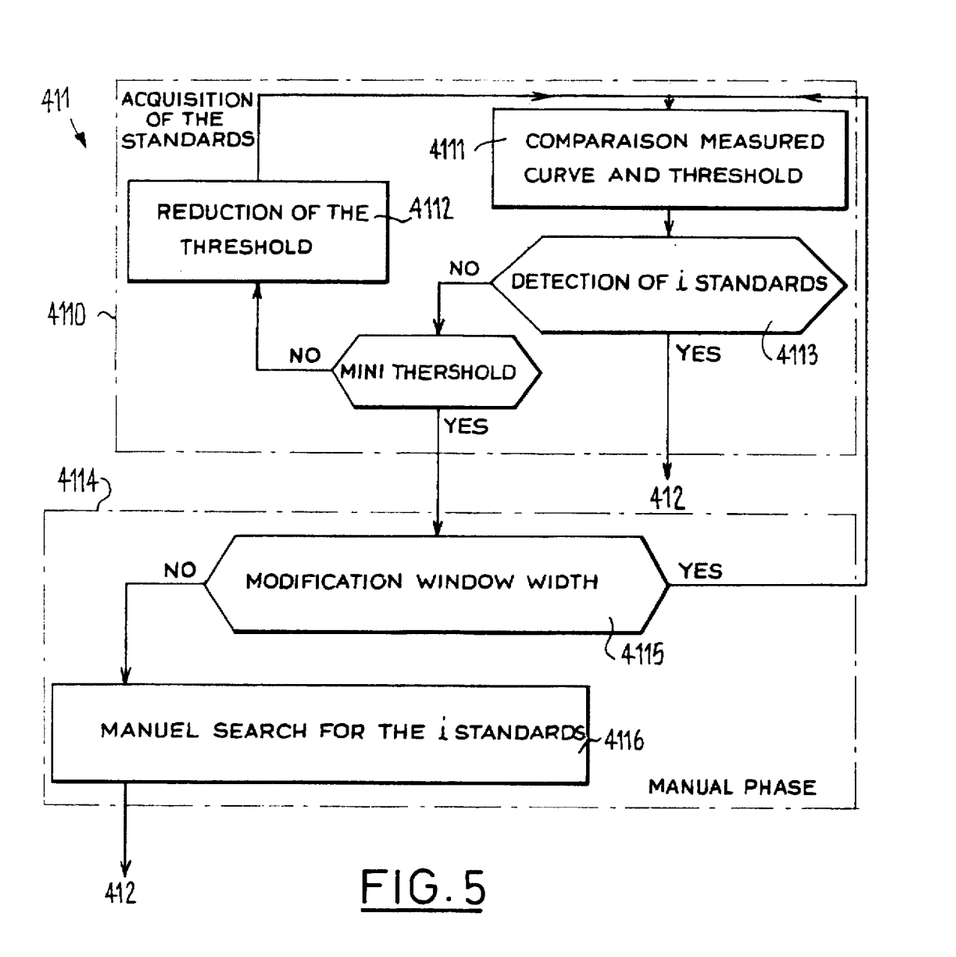

This stage 410 starts with stage 411 for acquisition of the i size standards in the corresponding file. This stage 411, which is detailed in FIG. 5, is carried out as follows.

In a first phase 4110, the apparatus automatically searches in a measurement window fixed by default, but which can be modified by the user, the i radiation peaks. This search is carried out by comparing (stage 4111),the intensity peaks measured with a threshold which is gradually reduced (stage 4112) until the i peaks are obtained (stage 4113).

If the first phase 4110 above does not make it possible to obtain the desired i peaks, the equipment passes to a second phase 4114 in which the user can either modify the width of the window at stage 4115 and restart the abovementioned automatic search phase 4110, or carry out a manual search (stage 4116) by identifying by any known means (for example with the aid of a pointer which moves on a screen) the desired peaks, on a representation of the measured curve visualized on screen.

As represented in the accompanying FIG. 4, once the size standards identified automatically or manually at stage 411 for the acquisition of the standards, this stage is followed by stage 412 for measuring the migration time ti of the standards of known length Li and then by stage 413 for calculation of the coefficients A, B and C for these standards based on this measurement.

The migration time ti of the size standards, measured at stage 412, corresponds to the time taken by them to reach the sensor of the detection set placed at the base of a supporting gel, from a time origin.

This time origin may correspond to the initiation of the electrophoresis, in which case the time constant to is zero.

The time origin can also be after the initiation of electrophoresis, in which case the time constant to is equal to the interval between the initiation of electrophoresis and the time origin considered. The user then introduces the value of this parameter once and for all. Subsequently, $t_o=0$ is used to simplify the mode of expression.

Figure 6:
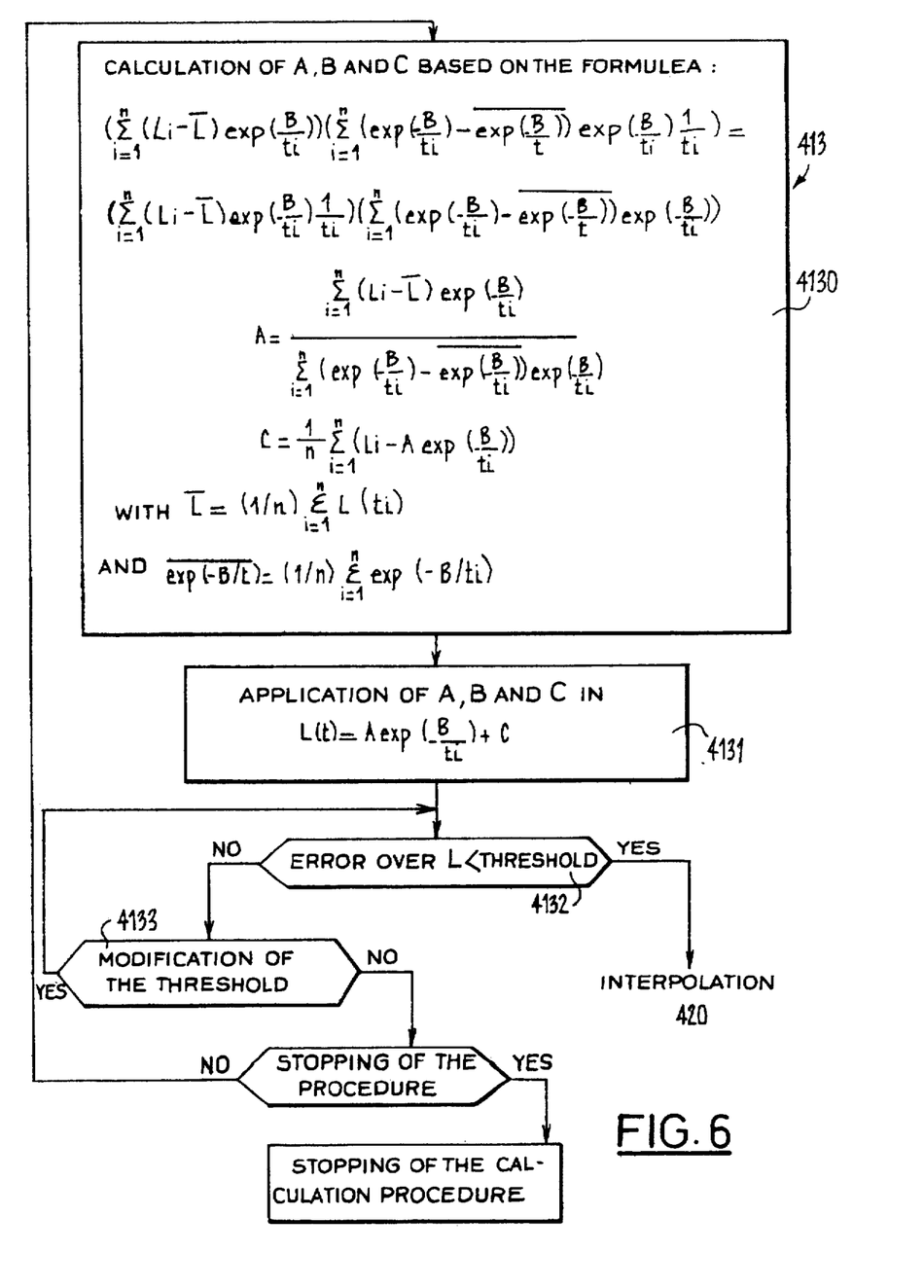

Stage 413 is illustrated in FIG. 6.

At stage 413, the coefficients A, B, C are first estimated (stage 4130) with the aid of the following least squares error function:

$$f(A,B,C) = \sum_{i=1}^{n} |L_i - (A\exp(-B/t_i) + C)|^2$$

in which n is the number of standard DNAs, by searching for the value of these coefficients A, B and C for which the partial derivative functions for A, B, C, of this function f(A, B, C) are zero.

A system of three equations of which one as a function only of B is thus obtained:

$$\left[ \sum_{i=1}^{n} (L_i - \overline{L})\exp(-B/t_i) \right] \times$$

$$\left[ \sum_{i=1}^{n} (\exp(-B/t_i) - \overline{\exp(-B/t)})\exp(-B/t_i)1/t_i \right] =$$

$$\left[ \sum_{i=1}^{n} (L_i - \overline{L})\exp(-B/t_i)1/t_i \right] \times$$

$$\left[ \sum_{i=1}^{n} (\exp(-B/t_i) - \overline{\exp(-B/t)})\exp(-B/t_i) \right]$$

$$A = \left[ \sum_{i=1}^{n} (L_i - \overline{L})\exp(-B/t_i) \right] / \left[ \sum_{i=1}^{n} (\exp(-B/t_i) - \overline{\exp(-B/t)})\exp(-B/t_i) \right]$$

$$C = (1/n) \sum_{i=1}^{n} [L_i - A\exp(-B/t_i)]$$

with as notation that:

$$\overline{X(t)} = (1/n) \sum_{i=1}^{n} X(t_i)$$

is the mean of X(1), . . . , X(n).

The first equation above therefore makes it possible to determine the value of the constant B.

And once the constant B is obtained, the constants A and C are obtained based on the last two equations above.

Once the coefficients A, B and C have been obtained at stage 4130 for the various standard lanes, the values A, B, C are applied to stage 4131 in the function f(A,B,C) or $L(t)=A \exp(-B/t)+C$ so as to check for each known set value Li of a standard that the difference between the theoretical size thus measured and the known set value Li is less than a given threshold equal to a predetermined number of bases (stage 4132).

If such is the case, the method in accordance with the present invention is continued by the interpolation stage 420.

If such is not the case, the calculation of the coefficients A, B and C is repeated, for the purpose of optimization, after modification of the threshold defined by a predetermined number of bases, by the user at stage 4133.

The aim of the interpolation stage 420 is to define the values of the migration times $t_i$ for the nonstandard markers for each lane for the measurement of samples based on the values measured for the standard lanes. The aim of this interpolation stage 420 is to reduce the measurement errors due to dispersion of the migration parameters along the width of the supporting gel.

This may be a linear interpolation.

However, within the framework of the present invention, a parabolic type interpolation can be carried out, for example the Simpson interpolation. The parabolic type interpolation indeed gives a result which is more precise than the linear interpolation.

Finally, at the stage 420, the values of the coefficients A, B and C are determined for each measurement lane from the $t_i$ values resulting from the interpolation, and this with the aid of the equations given above.

In practice, some equipments require that all the samples are not loaded onto the gel simultaneously. Most often, the supporting gels thus possess an even number of lanes having a common time origin and an uneven number of lanes also having a common time origin, but separated over time relative to the even number of lanes.

In this case, size standards are codeposited on the supporting gel respectively with the same origins as the various measurement lanes.

It is therefore necessary to calculate the coefficients A, B, C, for the size standards having different origins corresponding respectively to the even and uneven number of lanes and to carry out respective interpolations for the even and uneven number of measurement lanes respectively.

In other words, stages 410 and 412 are repeated for each measurement lane origin.

Once the coefficients A, B and C are known, and preferably stored for each measurement lane, stage 440 is carried out.

Figure 7:
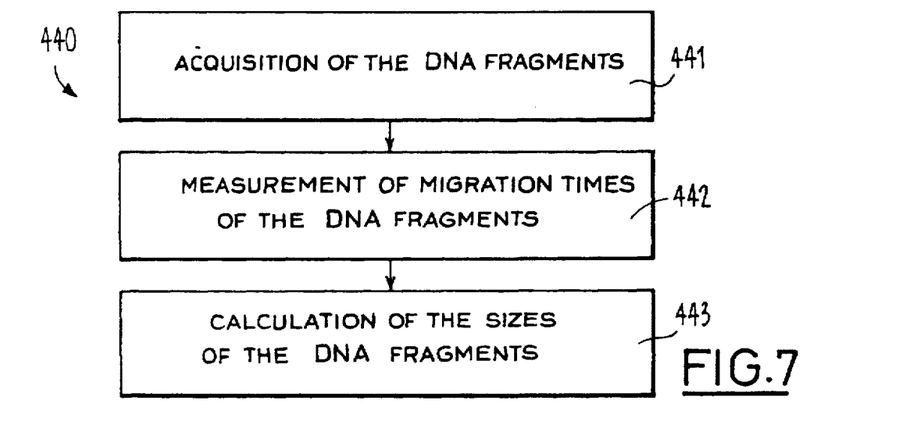
Figure 8:
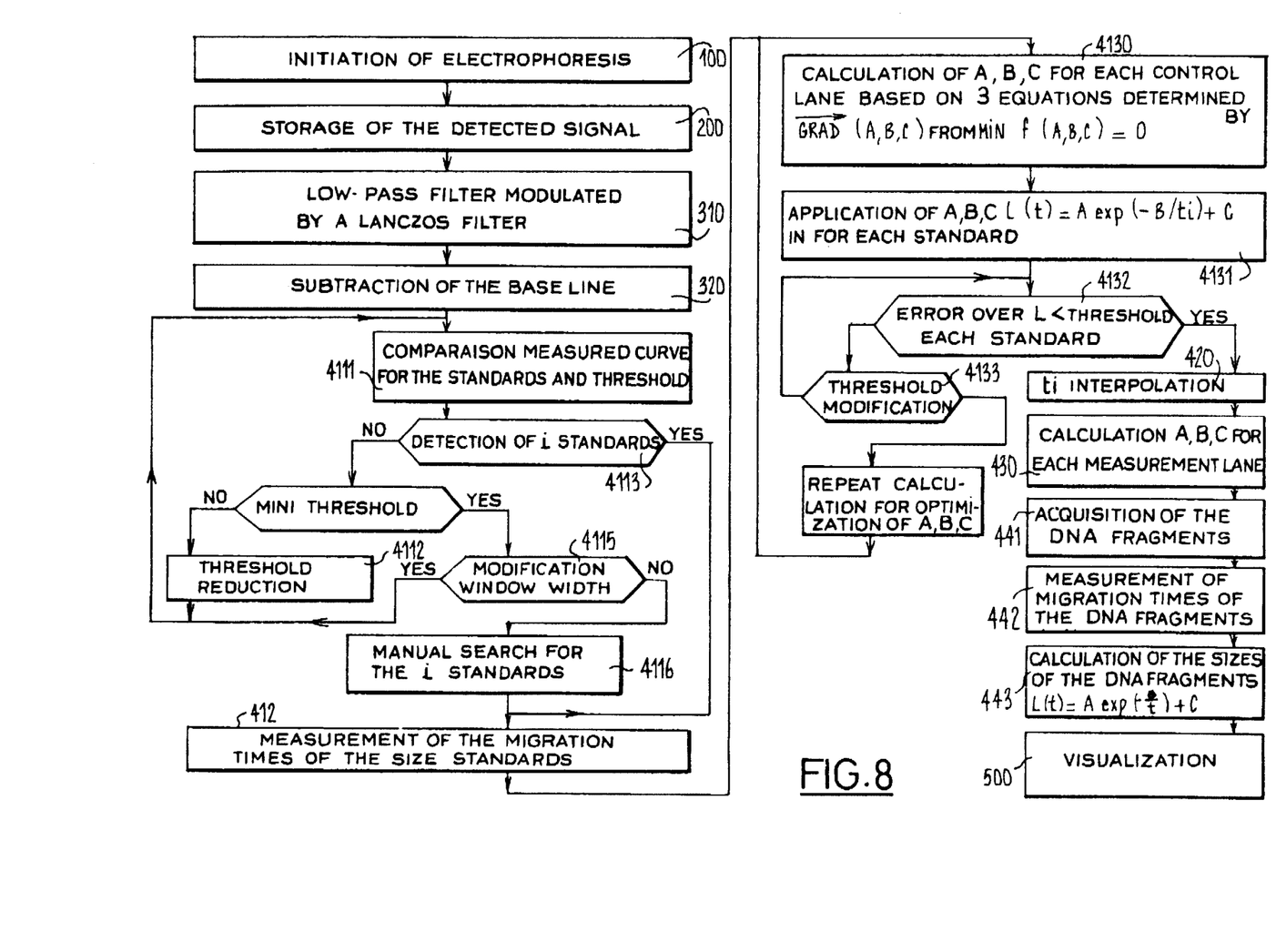
FIG. 8 represents a general flow diagram collating all the stages which will be described in the text which follows.

As illustrated in FIG. 7, this stage 440 is divided into three substages as follows:

a) acquisition of the peaks of the measurement signal corresponding to the DNA fragments (stage 441 in FIG. 7). This acquisition can be carried out automatically by comparing the amplitude of the measurement signal with a threshold. This threshold may be adjustable as well as the width of the window considered. The acquisition of the useful peaks can also be carried out manually. The operator then manually searches for the peaks of the signal corresponding to the DNA fragments, as described above and illustrated in FIG. 5 for the acquisition of the standards, b) measurement at stage 442 of the migration time of the DNA fragments, as described above at stage 412 for the standards, and finally c) calculation at stage 443 of the size of the various DNA fragments based on the equation:

$$L(t)=A\exp|-B/(t+t_0)|+C$$

Once the results have been fully calculated, their representation can be visualized in any appropriate form at stage 500.

For example, within the framework of a method for describing the repertoires of the immune system, the results can be illustrated in the form of a three-dimensional matrix of which two axes correspond to the primers V and J, whereas the third axis corresponds to the value of the size of the detected DNA segments.

The various analyzed samples which correspond to various lines of a section J/Size of the matrix correspond to respective J primers which are different from one line to another. Yet these various J primers have different yields. In order to allow comparison of the values represented from one line to another, the values measured, as a function of the yield of J primers, should therefore be standardized before carrying out the visualization.

Likewise, the V primers possess different yields. Consequently, to allow direct comparison of the values represented in the various sections J/Size, the values measured from one section to another are preferably standardized, based on quantitative measurements relative to the determination of the quantity of a DNA fragment of interest, before carrying out the representation.

The present invention makes it possible to greatly improve the precision of the measurement of the size of DNA fragments.

Indeed, while a rough comparison of the DNA fragments migrating by electrophoresis, with codeposited standards of known size, according to the state of the art, at best makes it possible to know the length of the DNA fragments with a precision of the order of 1 to 2%, according to the invention, on the other hand, the precision of the measurement is of the order of 0.3%.

Of course, the present invention is not limited to the specific embodiment which has just been described but extends to any variant in accord with the spirit thereof. In particular, in the case of the simultaneous use of several fluorophores emitting at different wavelengths, as indicated above, it is preferable to complement the method which has just been described by an initial process of elimination of the overlapping of the colors. It is known indeed that in the case of multiple fluorophores, the detected fluorescent signal gives a substantial contribution in the ad hoc color channel, but also, due to the imperfection of the filter situated in front of the sensor, contributions, indeed less substantial, in the other three channels. In order to eliminate these unwanted signals, the data recorded can undergo an operation which consists in multiplying the matrix of p lines (p representing the number of fluorophores used) and of n points (where n is the number of measurements carried out during the electrophoresis) by a square matrix (pxp) characteristic of the apparatus. Once this linear transformation has been carried out, the unwanted contributions to the signal for a color are practically completely eliminated.

I claim:

1. A method for determining the nucleotide size of DNA fragments separated by gel electrophoresis, the method comprising the stages of:

i) depositing DNA fragments to analyze on gel measurement lanes and co-depositing standards of known size on distinct control lanes of the same gel, ii) measuring the migration time of said standards of known size over a predetermined constant length on said control lanes, iii) interpolating on each of said measurement lanes the migration time of the standards of known size measured on said control lanes calculating migration parameters A, B, and C for each of said measurement lanes from the migration time values resulting from the interpolation, on the basis of a relation $$L_i = A \exp[-B/(t_i+t_o)] + C$$

wherein $L_i$ is the length of a standard of known size $t_i$ is the value of the migration time interpolated for said standard of known size on a measurement lane, $t_o$ is a time constant, and A, B, and C represent migration parameters, iv) measuring the migration time, over said predetermined constant length, for each detected DNA fragment on a measurement lane, and v) correlating the size of each detected DNA fragment with its migration time, on the basis of said migration parameters A, B, and C interpolated for each of said measurement lanes, on the basis of a relation $$L = A \exp[-B/(t_i+t_o)] + C$$

wherein

L represents the size of a DNA fragment, and t represents the migration time measured for said DNA fragment on a measurement lane.

2. The method of claim 1, wherein the value of the migration parameter coefficients A, B, and C are evaluated for the standards of known size, when the partial derivatives for A, B and C of the following function are zero:

$$\ln f(A,B,C) = \sum_{i=1}^{n} \{L_i - (A\exp(-B/t_i) + C)^2\} \ln f(A,B,C) = $$

$$\sum_{i=1}^{n} \{L_i - (A\exp(-B/t_i) + C)\}^2$$

in which $L_i$ represents the known lengths of the deposited size standards, $t_i$ represents the migration time of each of these known standards.

3. The method according to claim 2, wherein the migration parameter coefficients A, B and C are then applied, for each considered size standard, into the equation:

$$L(t) = A \exp[-B/(t+to)] + C,$$

the size values thus obtained being compared with the known size values so as to continue the process for calculating the migration parameter coefficients A, B and C, for the purpose of optimization, if the error between the measured size and the known size of the standards exceeds a predetermined threshold.

4. The method according to claim 2, wherein the migration parameters A, B and C are determined based on the following equations (a), (b) and (c):

$$\left\{ \sum_{i=1}^{n} (L_i - \overline{L})\exp(-B/t_i) \right\} \times \sum_{i=1}^{n} (\exp(-B/t_i) - \overline{\exp(-B/t)})\exp(-B/t_i)1/t_i = \quad (a)$$

$$\left\{ \sum_{i=1}^{n} (L_i - \overline{L})\exp(-B/t_i)1/t_i \right\} \times \sum_{i=1}^{n} (\exp(-B/t_i) - \overline{\exp(-B/t)})\exp(-B/t_i)$$

$$A = \left\{ \sum_{i=1}^{n} (L_i - \overline{L})\exp(-B/t_i) \right\} / \left\{ \sum_{i=1}^{n} (\exp(-B/t_i) - \overline{\exp(-B/t)})\exp(-B/t_i) \right\} \quad (b)$$

$$C = 1/n \sum_{i=1}^{n} \{L_i - A\exp(-B/t_i)\} \quad (c)$$

with the notation that $\overline{X(t)}$ designates the mean of the function X over the $t_i$ values:

$$\overline{X(t)} = (1/n) \sum_{i=1}^{n} X(t_i)$$

5. The method of claim 2, wherein the standards of known size are acquired by comparing a measurement curve detected in an adjustable measurement window with a threshold which is gradually reduced until desired i peaks are obtained.

6. The method of claim 1, wherein the interpolation is a linear interpolation.

7. The method according to claim 1, wherein the interpolation is of the parabolic type.

8. The method of claim 7, wherein the interpolation is a Simpson interpolation.

9. The method according to claim 1, wherein the gel used for the electrophoresis has a series of measurement lanes having time origins that are respectively separated and wherein the method comprises the stages of calculating the migration parameters for the standards of known size and in subsequently carrying out an interpolation of the $t_i$ positions obtained with the aid of the standards of known size, followed by a calculation of the corresponding migration parameters, on the measurement lanes, for each time origin of migration.

10. The method according to claim 1, wherein curves corresponding to said migration time measured for the DNA fragments are stored at the rate of one file per measurement lane.

11. The method of claim 1, wherein curves corresponding to said migration time measured for the DNA fragments are subjected to filtering.

12. The method of claim 11, wherein the filtering stage comprises a low-pass filtering.

13. The method of claims 11 or 12, wherein the filtering stage comprises a Lanczos filtering.

14. The method of claim 11, wherein the method comprises the additional stage of subtracting of a base line from a measured curve.

15. The method according to claim 1 wherein standards of known size are deposited on three control lanes: two side lanes and a center lane of the supporting gel.

16. The method of claim 1, wherein a plurality of standards of known size are deposited on each control lane.

17. The method of claim 16, wherein five standards of known size are deposited on each control lane.

18. A method for determining the nucleotide size of DNA fragments separated by gel electrophoresis, the method comprising the stages of:

depositing DNA fragments to analyze on gel measurement lanes and co-depositing standards of known size on distinct control lanes of the same gel, measuring the migration time of said standards of known size over a predetermined constant length on said control lanes, interpolating on each measurement lane the migration time of the standards of known size measured on said control lanes, and calculating migration parameters A, B, and C for each measurement lane, on the basis of a relation defining the length of a standard of known size in relation to the value of the migration time interpolated for said standard of known size on a measurement lane, and in relation to the migration parameters A, B and C, measuring the migration time, over said predetermined constant length, for each detected DNA fragment on a measurement lane, and correlating the size of each detected DNA fragment, with its migration time, on the basis of a relation defining the size of a DNA fragment in relation to the migration time measured for said DNA fragment on a measurement lane, and the migration parameters A, B and C.

19. A method for determining the nucleotide size of DNA fragments separated by gel electrophoresis, the method comprising the stages of:

depositing DNA fragments to analyze on gel measurement lanes and co-depositing standards of known size on distinct control lanes of the same gel, measuring the migration time of said standards of known size over a predetermined constant length on said control lanes, interpolating on each measurement lane the migration time of the standards of known size measured on said control lanes, calculating migration parameters A, B, and C for each measurement lane, from the migration time values resulting from the interpolation, on the basis of a relation $$L_i = A\, \exp[-B/(t_i+t_o)]+C$$

wherein $L_i$ is the length of a standard of known size, $t_i$ is the value of the migration time interpolated for said standard of known size on a measurement lane, $t_o$ is a time constant, and A, B, and C represent migration parameters, wherein the value of the migration parameters A, B and C are evaluated, when the partial derivatives for A, B and C of the following function are zero:

$$f(A,B,C) = \frac{1}{n} \sum_{i=1}^{n} \left\{ L_i - \left(A \exp\left(-\frac{B}{t_i+t_o}\right) + C\right) \right\}^2$$

wherein n is the number of DNA fragments in the standards measuring the migration time, over said predetermined constant length, for each detected DNA fragment on a measurement lane, and correlating the size of each detected DNA fragment with its migration time, on the basis of said migration parameters A, B, and C interpolated for the measurement lanes, on the basis of a relation $$L = A\, \exp[-B/(t+t_o)]+C$$

wherein

L represents the size of a DNA fragment and t represents the migration time measured for said DNA fragment on a measurement lane.

20. A method for determining the nucleotide size of DNA fragments separated by gel electrophoresis, the method comprising the stages of:

depositing DNA fragments to analyze on gel measurement lanes and co-depositing five standards of known size on three distinct control lanes of the same gel: two side lanes and a center lane, measuring the migration time of said standards of known size over a predetermined constant length on said three control lanes, interpolating on each measurement lane the migration time of the standards of known size measured on said control lanes, calculating migration parameters A, B, and C for each measurement lane, from the migration time values resulting from the interpolation, on the basis of a relation $$L_i = A\, \exp[-B/(t_i+t_o)]+C$$

wherein $L_i$ is the length of a standard of known size, $t_i$ is the value of the migration time interpolated for said standard of known size on a measurement lane, $t_o$ is a time constant, and A, B, and C represent migration parameters, wherein the value of the migration parameters A, B and C are evaluated, when the partial derivatives for A, B and C of the following function are zero:

$$f(A,B,C) = \frac{1}{5} \sum_{i=1}^{5} \{L_i - (A\exp(-B/(t_i+t_o))+C)\}^2$$

measuring the migration time, over said predetermined constant length, for each detected DNA fragment on a measurement lane, and correlating the size of each detected DNA fragment with its migration time, on the basis of said migration parameters A, B, and C interpolated for the measurement lanes, on the basis of a relation $$L = A\, \exp[-B/(t+t_o)]+C$$

wherein

L represents the size of a DNA fragment and t represents the migration time measured for said DNA fragment on the measurement lane.

* * * * *

UNITED STATES PATENT AND TRADEMARK OFFICE
CERTIFICATE OF CORRECTION

PATENT NO. : 5,795,455
DATED : August 18, 1998
INVENTOR(S) : Pannetier It is certified that error appears in the above-identified patent and that said Letters Patent is hereby corrected as shown below:

Title page, Item
In [30], add -- July 2, 1993 [ WO ]    WIPO    ..................PCT/FR93/00675 -- .

Title page, Item
In [56], under the heading "Other Publications," within the citation for A.V. Carrano et al., delete "High-Resolution Fluoreescence" and insert -- "High-Resolution Fluorescence -- .

Signed and Sealed this

Thirteenth Day of February, 2001

*Attest:*

NICHOLAS P. GODICI

*Attesting Officer*    *Acting Director of the United States Patent and Trademark Office*